(12) United States Patent
Kawanishi et al.

(10) Patent No.: US 7,297,548 B2
(45) Date of Patent: Nov. 20, 2007

(54) SOLID-PHASE SACCHARIDE SENSING COMPOUNDS

(75) Inventors: Tetsuro Kawanishi, Kanagawa (JP); Matthew Albert Romey, Long Beach, CA (US); Mark Z. Holody, Irvine, CA (US); Peter C. Zhu, Irvine, CA (US); Seiji Shinkai, Fukuoka (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 45 days.

(21) Appl. No.: 10/551,032

(22) PCT Filed: Mar. 28, 2003

(86) PCT No.: PCT/US03/09380

§ 371 (c)(1),
(2), (4) Date: Sep. 27, 2005

(87) PCT Pub. No.: WO2004/096817

PCT Pub. Date: Nov. 11, 2004

(65) Prior Publication Data

US 2006/0223189 A1    Oct. 5, 2006

(51) Int. Cl.
*G01N 33/00* (2006.01)

(52) U.S. Cl. ............................. 436/90; 562/7
(58) Field of Classification Search ............. 436/90; 562/7
See application file for complete search history.

(56) References Cited

U.S. PATENT DOCUMENTS

| | | | |
|---|---|---|---|
| 6,002,954 A | | 12/1999 | Van Antwerp et al. |
| 6,366,793 B1* | | 4/2002 | Bell et al. .................. 600/317 |
| 6,794,195 B2* | | 9/2004 | Colvin, Jr. .................. 436/95 |
| 2002/0090734 A1* | | 7/2002 | Daniloff et al. .................. 436/95 |
| 2002/0094586 A1* | | 7/2002 | Daniloff et al. .................. 436/518 |

FOREIGN PATENT DOCUMENTS

| | | | |
|---|---|---|---|
| GB | 2284809 | * | 6/1995 |
| WO | WO 01/20334 A1 | | 3/2001 |
| WO | WO 0118543 | * | 3/2001 |
| WO | WO 02/12251 A1 | | 2/2002 |
| WO | WO 02054067 | * | 7/2002 |
| WO | WO 02057788 | * | 7/2002 |

OTHER PUBLICATIONS

Linnane et al., A Sweet Toothed Saccharide (PET) Sensor, Tetrahedron Letters, 1995, 36, (48) 8833-8834.*

James et al., Novel Saccharide-Photoinduced Electron Transfer Sensors Based on the Interaction of Boronic Acid and Amine, Journal of the American Chemical Society, 1995, 117 (35), 8982-8987.*

James et al., A Diboronic Acid 'Glucose Cleft' and A Biscrown Ether 'Metal Sandwich' are Allosterically Coupled, Journal of the Chemical Society, Chemical Communications, 1995, (14), 1483-1485.*

* cited by examiner

*Primary Examiner*—Johann Richter
*Assistant Examiner*—Chukwuma Nwaonicha
(74) *Attorney, Agent, or Firm*—Buchanan Ingersoll & Rooney PC

(57) ABSTRACT

The present invention provides solid-phase saccharide dyes. The dyes are bisboronic acids covalently bonded to a solid substrate. The dyes selectively conjugate with saccharides, particularly glucose, and register a signal. The signal is proportional to the quantity of saccharide. Thus, the dyes of the present invention are useful for measuring and monitoring saccharide levels, particularly in biological fluids such as blood.

28 Claims, 17 Drawing Sheets

Fluorescent Property of Single-Arm Fluorophore Linked Sensor

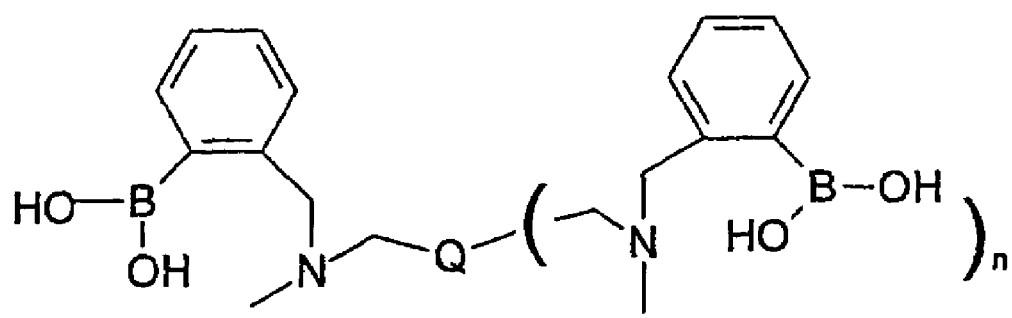
FIGURE 1A: Shinkai Dye
Q is a fluorophore; n = 0 or 1
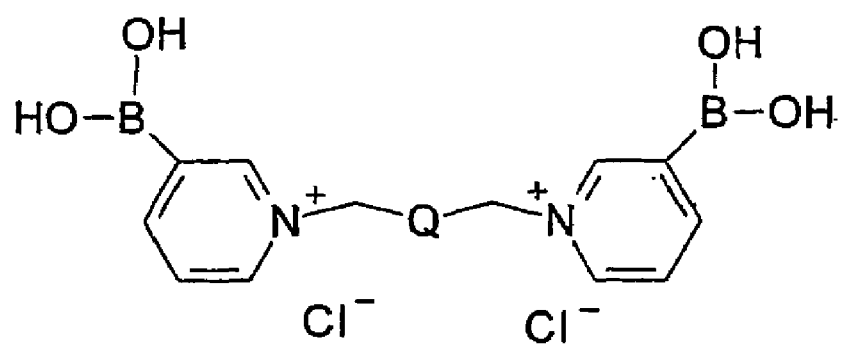
FIGURE 1B: Norrild Dye
Q is a fluorophore

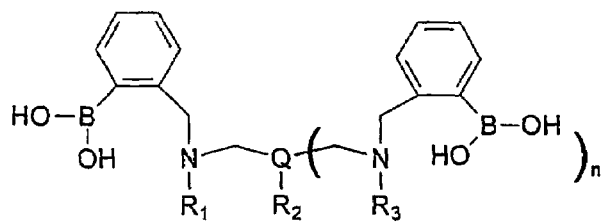
FIGURE 2A: Shinkai Dye
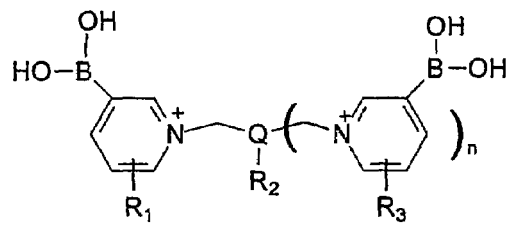
FIGURE 2B: Norrild Dye
Figure 2: Q is a fluorophore; and n is an integer from 0 to 1. One or more of $R_1$, $R_2$, $R_3$, is a linker arm attached to solid phase, and the rest are each independently selected from the group consisting of hydrogen, alkyl, alkenyl, aryl, arylalkyl, acyl, and substituted alkyl.

Napthalene  Anthracene  Pyrene  1,2 - Benzanthracene  2,3 - Benzanthracene

Synthesis
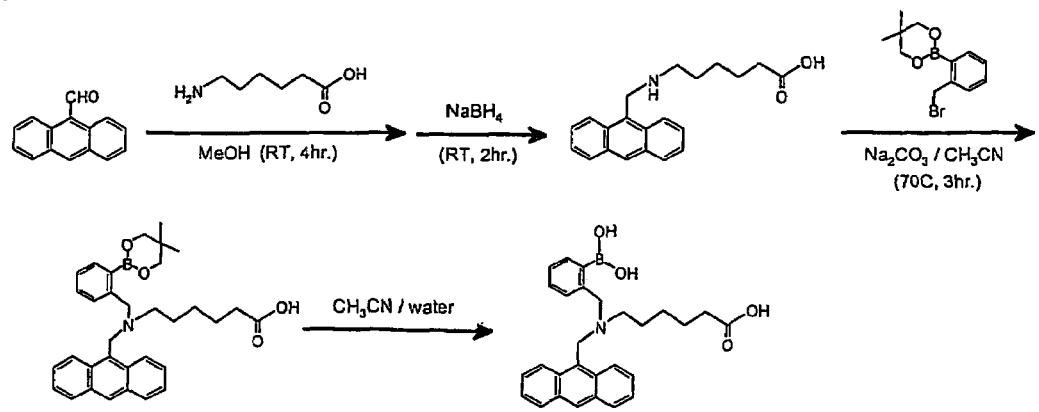
Immobilization
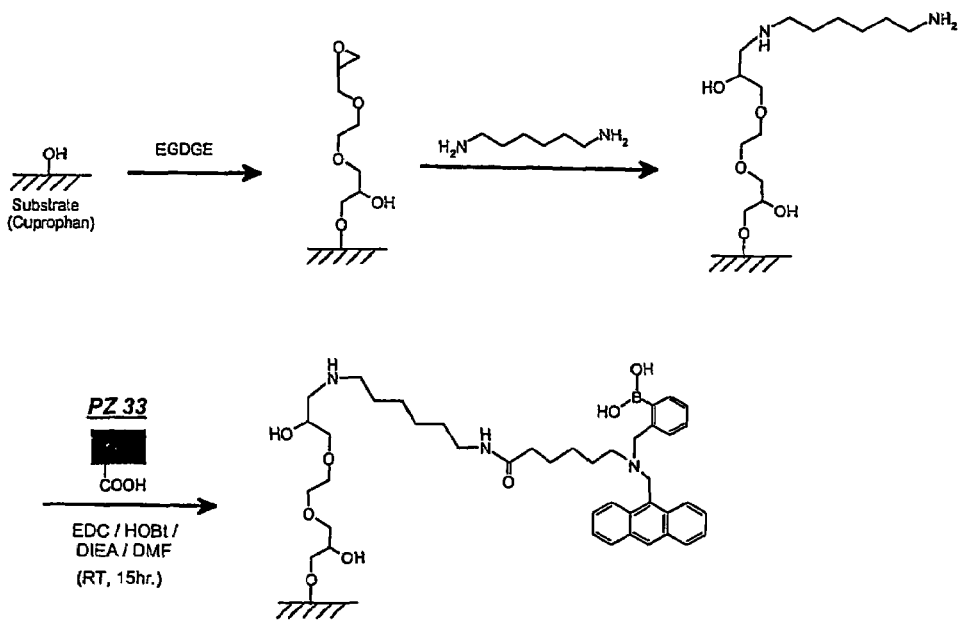
FIGURE 4

Synthesis
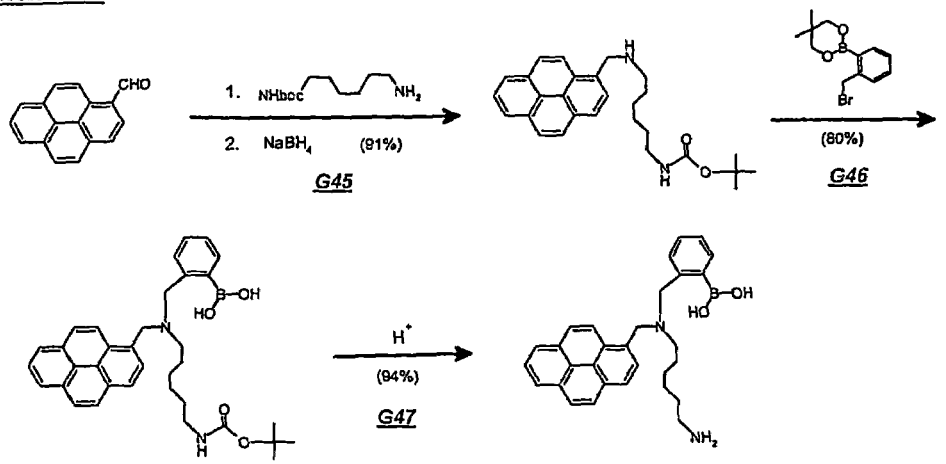
Immobilization
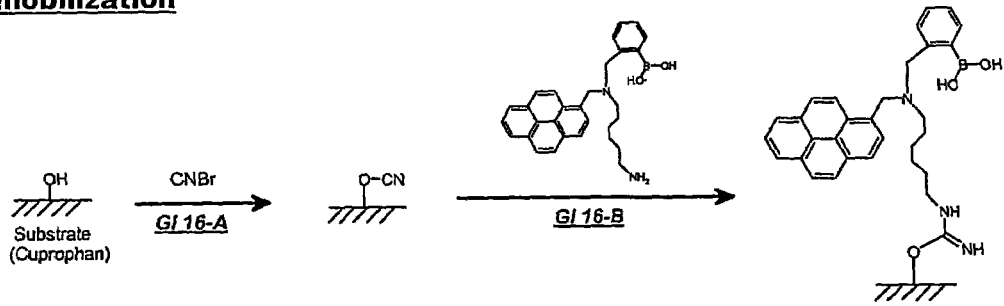
FIGURE 5

Glucose Response of Saccharide Sensor Gl 16-B

Syntheses
A. Shinkai Molecule with Di(aminoalkyl) Arms
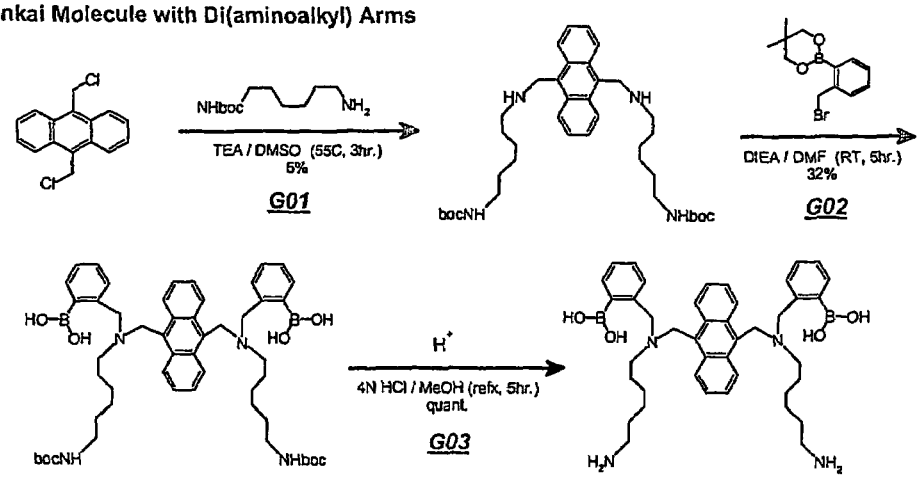
B. Shinkai Molecule with Di(carboxylalkyl) Arms
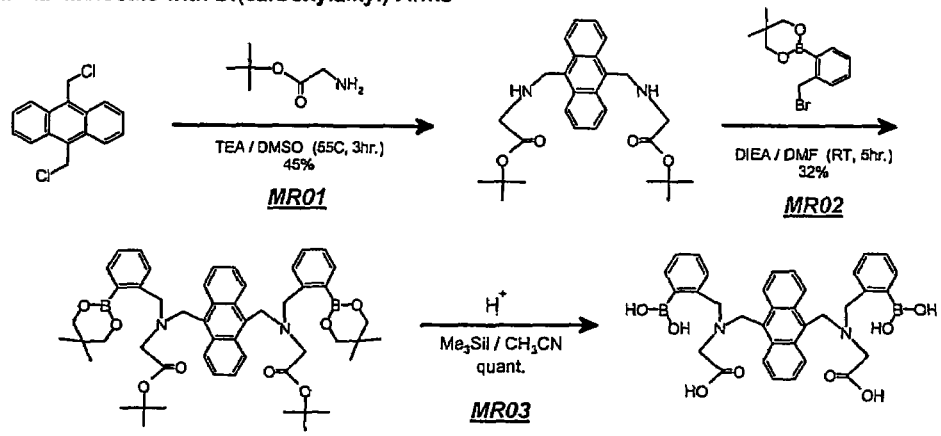
FIGURE 7

GI 02 Coupling to carboxyl group

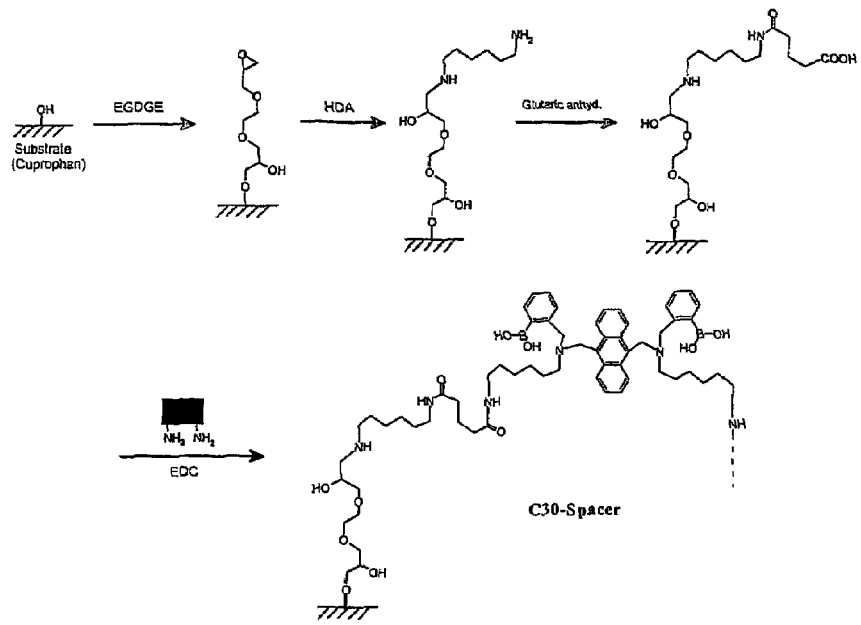

GI 04 Coupling to CNBr activated membrane

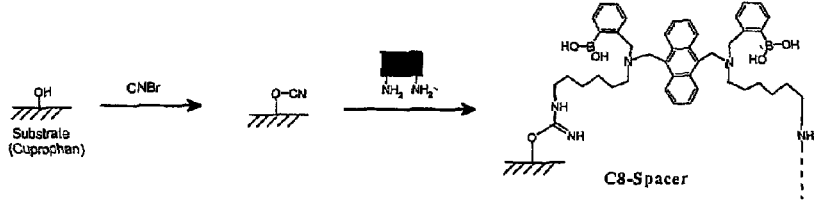

FIGURE 8

Immobilization: Shinkai Molecule with Di(aminoalkyl) Arms
Coupling through carboxyl and CNBr activated substrates GI 02 : Carboxyl activated regenerated cellulose film coupled to the amino-terminated dye in the presence of a condensation reagent such as carboimide (EDC).

GI 04 : Cyanogen bromide activated regenerated cellulose film coupled to amino-terminated dye.

Coupling to EGDGE Activated Membrane

GI 05 : Amino-terminated dye is coupled to epoxy activated regenerated cellulose film.

GI07 Coupling to carboxyl group

Shinkai Molecule with Di(carboxylalkyl) Arms

GI 07 : The carboxyl-terminated dye is coupled to amino activated regenerated cellulose film.

Synthesis
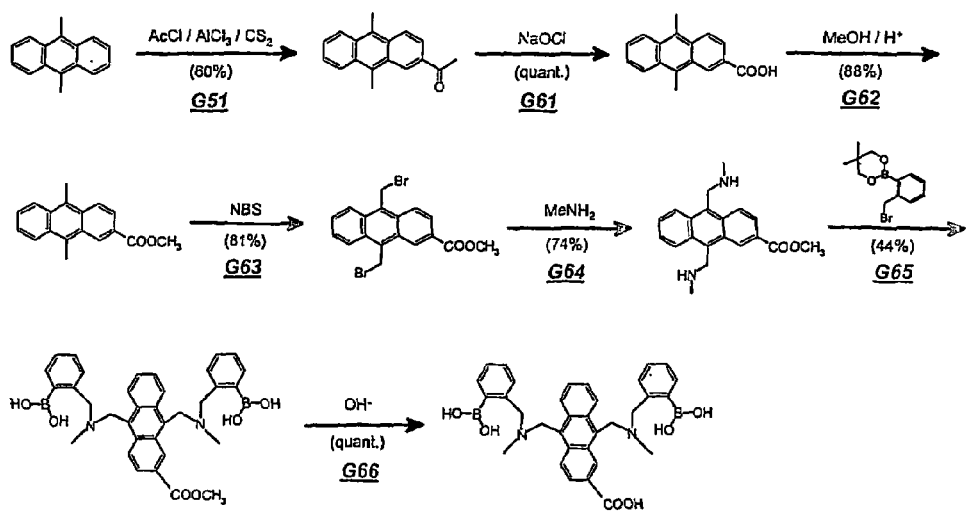
Immobilization
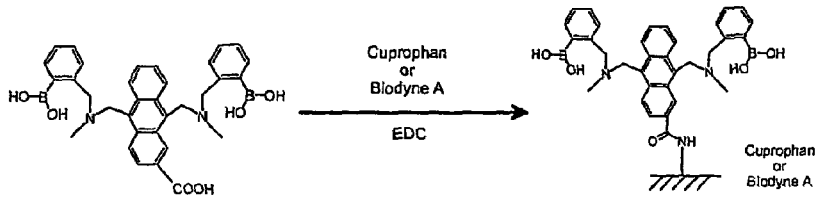
FIGURE 16

Fluorescent Property of Single-Arm Fluorophore Linked Sensor

Glucose Response of Single-Arm Fluorophore Linked Sensor

Synthesis
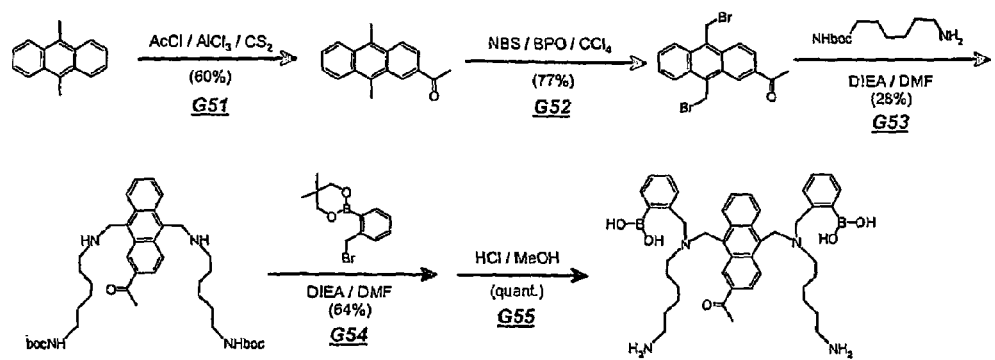
Immobilization
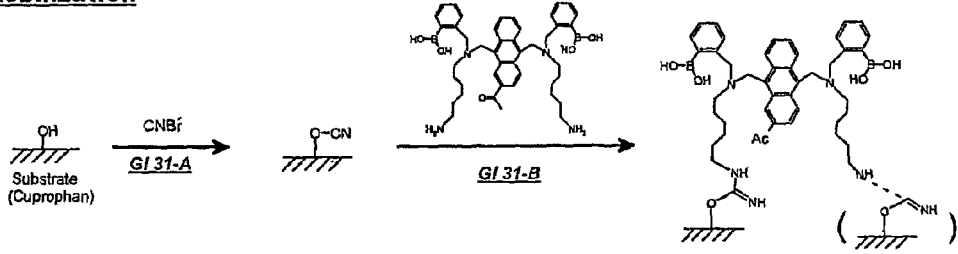
FIGURE 19

Fluorescent Property of Acetylated and Non-acetylated Anthracene Sensor

Glucose Response of Acetylated Anthracene Saccharide Sensor

SOLID-PHASE SACCHARIDE SENSING COMPOUNDS

FIELD OF THE INVENTION

The present invention is directed to novel bisboronic acid-based saccharide sensors. The sensors are of the fluorescent photoinduced electron transfer (PET) type. The sensors can be immobilized on polymer substrates, and fabricated into saccharide sensors in medical devices used for monitoring saccharide levels in patients.

BACKGROUND OF THE INVENTION

Saccharides are nature's conveyors of energy, and are essential for cell survival. James, T. D. et al., *J. Am. Chem. Soc.*, 117, 8982-8987 (1995) (citing Robertson, R. N., *The Lively Membranes*, Cambridge University Press, New York, 1983). Defects in glucose transport are associated with various disease states, and fluctuations in glucose levels can be symptomatic or predictive of acute, as well as chronic conditions. Id. Thus, the ability to detect and monitor glucose levels in animals, particularly humans, is extremely important.

Molecular recognition of saccharides or sugars, such as glucose, has proven to be a reliable detection mechanism. Perhaps the most reliable and efficient systems for such detection are those exploiting the phenomena of intramolecular electron transfer, also called photoinduced electron transfer (PET).

Systems capable of effecting such molecular recognition exhibit both structural and fluorescence changes upon saccharide binding. The change in fluorescence is proportional to the concentration of saccharide in the sample, and so these sensors or dyes can be used for quantitative measurement.

Among the more popular of these sensors are boronic acid based saccharide sensors. Boronic acid sensors effect reversible formation of strong covalent bonds with the diol functionalities of carbohydrates in the form of cyclic esters. These sensors are superior to other sensor systems involving weaker noncovalent or hydrogen bonded interactions.

Boronic acid sensors are not without their own shortcomings. The design of a fluorescent sensor based on the boronic acid-saccharide interaction proved difficult due to the lack of sufficient electronic changes found in either the boronic acid moiety or the saccharide moiety. *J. Am. Chem. Soc.*, 117, at 8983. Shinkai's group showed that those disadvantages could be overcome by modifying the boronic acid binding site to create an electron rich center around the boronic acid moiety by, e.g., adding a tertiary amine, which formed an intramolecular five membered ring with the boronic acid moiety. Id. They then showed that the 9,10-bis-(aminomethyl)-anthracene skeleton provided a glucose selective sensor by producing a perfect glucose-selective cleft within the molecule. Id. These efforts resulted in the so called "Shinkai dyes" (FIG. 1A).

Building on the work of Shinkai's group, Norrild's group sought to create dyes that were both specific for the glucose molecule relative to other saccharides, and capable of binding glucose at neutral pH. Eggert et al, *J. Org. Chem.*, 64, 3846-3852, 1999. To bind glucose at neutral pH, the boronic acid must have a $pK_a \leq 7$. Devising such a boronic acid sensor dye proved to be a major problem in that most of the dyes proposed up to that point had $pK_a$ in the 8 to 10 range.

Norrild and co-workers chose 3-pyridineboronic acid for its especially low $pK_a$, and produced a bis-boronic acid comprising two 3-pyridineboronic acid moieties grafted onto an anthracene moiety. The resulting "Norrild" dyes (FIG. 1B) possessed the requisite low $pK_a$ values and water solubility with a structurally optimized design for selective glucose binding. These dyes were reported to possess a selective fluorescence response to glucose compared to fructose and galactose.

Both the Shinkai and Norrild type dyes are solution-based systems. The solution-based system affords great freedom for the intramolecular changes that signal saccharide binding. However, certain applications require a solid-phase dye. Immobilization will likely reduce molecular freedom and alter the electrochemistry. This will in turn affect the fluorescence of the molecule, and might diminish its utility. That is, immobilization can reduce the fluorescence intensity or reduce the fluorescent response in the physiological testing region.

Saccharide sensors within the art generally have one or more shortcomings. For example, known sensors are capable of producing a discernible signal in response to saccharide binding, but do not provide the desired specificity for glucose relative to other saccharides.

Additionally, the known saccharide sensors lack the desired quantitative response. That is, as the concentration of saccharide increases, fluorescence increases only modestly. Preferably, the slope of relative fluorescence intensity as a function of saccharide concentration is high, and remains high throughout the range of saccharide concentration that is of physiological significance. Sensors exhibiting high slope of intensity, as a function of concentration will produce a signal that is more reliable and more readily discernible thereby substantially reducing costs of production.

Further, the use of fluorescence as a detection or diagnostic device benefits from a significant Stokes' shift. The Stokes' shift derives from the empirical law that the emission wavelength of a fluorescent material is longer than that of the radiation used to excite fluorescence. If the Stokes' shift is small, the excitation and emission peaks are in close proximity, and it is necessary to resort to sophisticated optics and filtering devices to distinguish the two. As the Stokes' shift increases, the wavelength of the excitation peak moves further away from emission peak, and the reliance on filters to distinguish the two is reduced. This again, facilitates a more economical device.

Attempts to improve the glucose specificity of boronic acid based saccharide sensors, and/or improve the fluorescence properties of the sensor, and/or immobilize those traditionally solution-based systems on polymeric substrates have met with only limited success. E.g., Arimori, S., et al, *Chem. Commun.*, 2001, 1836-1837.

One of the principle objectives in devising a saccharide dye is to create a dye that demonstrates a steep slope for the curve of relative intensity versus saccharide concentration. Shinkai and Norrild have shown that it is possible to create saccharide dyes that, in a solution-based system, have that steep slope. Subsequent work, however, has shown that the covalent linkage of those dyes to a solid substrate can result in a substantial reduction in that slope. As yet, there is nothing within the art disclosing saccharide dyes covalently attached to solid-phase that do not suffer a substantial loss or elimination of that slope.

Some workers have attempted to extend the work of Shinkai and Norrild to achieving solid-phase construction, but fail to produce a system that can be used in direct blood contact, or in ex-vivo approaches, in which blood is circulated outside the body. WO 01/74968 A2 and WO 01/20334 A1. That work focuses on the use of an allegedly solid-phase saccharide dye of the Shinkai type to be inserted in a patient under the skin to measure saccharide in interstitial fluid spaces. See also U.S. Pat. Nos. 6,002,954, and 6,011,984.

There is a need within the art for saccharide dyes that have high glucose specificity. Ideally, such high specificity glucose sensors will demonstrate improved fluorescence properties. There is also a need in the art for dyes that retain such specificity and fluorescence properties when immobilized by covalent attachment to a solid substrate.

BRIEF DESCRIPTION OF THE DRAWINGS

FIG. 1A is a structural representation of a Shinkai dye; and FIG. 1B is a Norrild Dye.

FIG. 2A is a structural representation of an immobilized Shinkai-type Dye; and FIG. 2B is an immobilized Norrild-type Dye.

FIG. 4 is a synthetic scheme for an anthracene-containing Shinkai-type monophenylboronate compound of the present invention, including a method for immobilizing it on a solid-phase.

FIG. 5 is a synthetic scheme for a pyrene-containing Shinkai-type mono-phenyl boronate compound of the present invention with a single linker arm.

FIG. 7 is a synthetic scheme for making and immobilizing a Bis-phenylboronate anthracene-containing Shinkai-type dye.

FIGS. 8-10 are synthetic schemes for immobilizing a Bis-phenylboronate anthracene-containing Shinkai-type dye.

FIG. 16 illustrates a scheme for making and immobilizing a Bis-phenylboronate Shinkai-type dye on a solid-phase material with a single linker arm covalently attached directly to the fluorophore.

FIG. 19 illustrates a scheme for making and immobilizing a Bis-phenylboronate Shinkai-type dye having dual arm immobilization and an acetylated fluorophore.

DETAILED DESCRIPTION OF THE INVENTION

Figure 3:
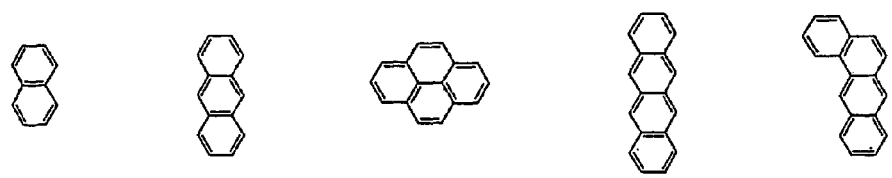
FIG. 3 is a structural representation of various fluorophores useful in the compounds of the present invention.

The present invention provides solid-phase saccharide dyes, and methods for making them. The present invention further provides devices incorporating those dyes. The devices include liquid conduits incorporating the solid-phase dyes of the instant invention for detecting and monitoring saccharide levels in a fluid. Exemplary fluids are blood, blood fractions, plasma, urine, and other biological fluids or extracts of biological components.

For purposes of the present invention, the term "saccharide dye" is used to refer to molecules capable of reversibly binding a saccharide such that the molecule exhibits a discernible physicochemical change associated with the binding and/or release of the saccharide. In preferred embodiments, the physicochemical change is readily discernible by spectroscopic methods, e.g., fluorescence, phosphorescence, colorimetric, etc. The physicochemical change can thus be monitored by changes in a signal molecule or moiety, e.g., a fluorophore or phosphorescent species.

The term "solid-phase saccharide dye" is used to refer to a saccharide dye that is covalently attached to a solid substrate or solid-phase material. Exemplary substrates are natural or synthetic organic polymers and inorganic substrates such as ceramics and glass.

Polymers known to be biocompatible are preferred. Polymers generally recognized as biocompatible include cellulose (e.g., Cuprophan), polystyrene, polyamide, polyethersulfone, polyethyleneglycol, polypropyleneglycol, polyvinyl alcohol, polysiloxane, nylon (e.g., Biodyne), and copolymers thereof. Particularly preferred are polymers known to be highly biocompatible, e.g., cellulose, polyethersulfone, polyethylene glycol, polypropylene glycol, and polyvinyl alcohol.

Also preferred are polymers having available functional groups that facilitate covalent attachment to a functionalized hydrocarbon linker arm on the glucose sensor. Preferred functional groups in the polymer substrate are hydroxyl, carboxyl, aldehyde, ketone, amine, amide, and cyano.

The solid-phase to which the saccharide dye is covalently attached can be fabricated in many different forms, e.g., films, sheets, pellets, flakes, granules, microparticles, microspheres, etc. The preferred physical shape and size of the solid-phase will be largely dependent on the end product.

In one embodiment, the saccharide dye is immobilized on a solid substrate. The solid substrate is contacted with a fluid under investigation. The fluid can be a gas, vapor, or liquid. Fluid contact can be achieved by any conventional means, e.g., fluid bed, column, or conduit. Preferably, the fluid is a liquid such as blood, a blood fraction, plasma, urine, etc. As the fluid contacts the saccharide dye on the solid substrate, the dye signals the presence or absence, and preferably the quantity, of the analyte, e.g., glucose. The signal can be detected by colorimetric or spectroscopic means. The signal can be fed to conventional devices for display as by real-time read-out or by recording and displaying cumulative results as by charts, tables, or graphs.

In another embodiment, the product is a conduit for monitoring saccharide levels, particularly glucose, in blood. The saccharide dye is immobilized on a polymeric substrate. The polymeric substrate is incorporated in a conduit such that the saccharide dye is in contact with the fluid flowing through the conduit. The conduit can be incorporated into an in-line flow path for blood or some other biological fluid, ex-vivo or in-vivo. The dye is scanned or monitored to detect the level of analyte in the blood or other biological fluid.

In preferred embodiments, the saccharide dye includes an aromatic polycyclic fluorophore. Particularly preferred is anthracene. The dye can be attached to a solid-phase via linkages at nitrogen, the pyridine, or aromatic rings of fluorophore in the manner shown in FIG. 2.

The fluorescent property of a dye, such as excitation and emission wavelength, depends on the fluorophore, particularly the arrangement of the aromatic rings and the substitution on the rings. Elongation of aromatic conjugated double bond system, or introduction of halogen, acyl, alkyloxy, nitro, carboxylic acid, or carboxylic acid ester into the rings can improve the fluorescent property of a dye, and can effect a red shift or Stokes' shift. For example, our results show that the use of pyrene as a fluorophore for a Shinkai-type dye, or acetyl substitution of anthracene for a Shinkai-type dye, brought greater fluorescence (relative intensity) than an original or soluble Shinkai dye. These improvements give rise to increased sensitivity and accuracy in sensor performance.

More particularly, the manipulations described herein afford solid-phase saccharide dyes wherein the excitation-emission differential of the conjugated dye is about 40 nm or greater. As used herein, the term conjugated dye means a saccharide dye wherein the saccharide binding portion of the dye is occupied by a saccharide such that a signal is effected. In the case of a fluorescent dye, the conjugated dye will fluoresce indicating the presence of saccharide. Preferred solid-phase saccharide dyes of the present invention have an excitation-emission differential upon saccharide conjugation of about 45 nm or greater. Particularly preferred solid-phase saccharide dyes of the present invention have an excitation-emission differential upon conjugation of about 70 nm or greater.

Additionally, the solid-phase saccharide dyes of the present invention have increased fluorescence upon saccharide binding. Preferred embodiments have relative intensity across the physiologic range of about 1.5 or greater. For purposes of the present invention, the physiological range of glucose is from about 50 to about 500 mg/dl in blood, blood fractions, or plasma. More preferred embodiments are capable of exhibiting relative intensity of about 2.0 or greater across the physiological range of glucose.

With reference to FIG. 2, both mono(benzene boronic acid) and bis(benzene boronic acid) are useful saccharide sensing molecules that can be immobilized on a substrate. The saccharide binding and signal portions of the molecule are bound to the solid-phase by means of linker arms. The linker arms and non-linker substituents are saturated or unsaturated hydrocarbons that can be otherwise functionalized. The hydrocarbon chain can be branched or straight chain, and the length can vary quite extensively. Preferably, the chain length will be about $C_{30}$ or fewer. The functional groups can be maintained or protected for covalent attachment of the solid-phase and the dye. Alternatively, other functional groups can be employed for derivatizing the solid-phase and/or the dye prior to covalent attachment of the two.

Although the linker arms and non-linker substituents are described herein as hydrocarbon chains, as used herein the term includes functionalized hydrocarbons and includes at least alkyl, alkenyl, alkynyl, aldehydes, ketones, ethers, esters, amines, amides, carboxyl, halo, aryl, acyl, and like moieties. The various functional groups can occur in combination within a hydrocarbon linker arm, and can be internal to the hydrocarbon chain or at or about its terminus. The linker arm and non-linker hydrocarbons of the present invention can be straight-chain alkyl groups, or they can be functionalized or branched at various points along the hydrocarbon chain.

Preferably, a hydrocarbon of a linker arm is an alkyl, an amine, an amide, a ketone, an ether, an ester, and/or a combination thereof.

Preferred embodiments of the present invention include compounds of Formula 1:

Formula I

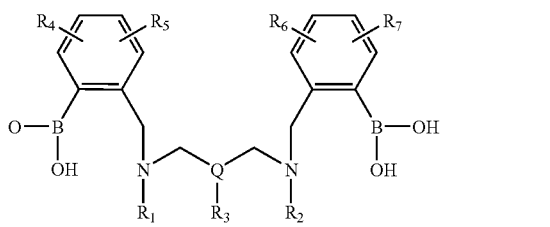

According to Formula 1, at least one or more of $R_1$, $R_2$, and $R_3$ are linker arms for covalent attachment to solid-phase; and the remaining groups are non-linker substituents selected from among hydrogen, and saturated and unsaturated hydrocarbons that can be further activated with various functional groups. The hydrocarbon chain length of a non-linker substituent $R_1$, $R_2$, or $R_3$ can also vary, but will likewise preferably be about $C_{30}$ or fewer.

The substituents $R_4$, $R_5$, $R_6$, and $R_7$ are selected from the group consisting of hydrogen, alkyl, alkenyl, aryl, arylalkyl, substituted alkyl, acyl, alkyloxy, and halogen. The substituents $R_4$ and $R_5$, and $R_6$ and $R_7$ together can form condensed aromatic rings such as naphthalene, anthracene, and the like. In preferred embodiments, the bis-boronic acid compounds are symmetric around Q and comprise an aromatic ring or fused polycyclic aromatic ring.

Q is the signaling moiety that provides a detectable signal for monitoring saccharide binding and/or release. Preferably Q is a fluorophore, a phosphorescent moiety, a colorimetric moiety, or a luminescent moiety.

Q is preferably a fused polycyclic aromatic fluorophore. Preferred examples are naphthalene, anthracene, pyrene, 1,2-benzanthracene, and 2,3-benzanthracene, as shown in FIG. 3. Any of the rings can be substituted with one or more functional groups. In one preferred embodiment, Q is a fluorophoric species comprising acetylated anthracene.

Other embodiments of the present invention are illustrated in FIG. 2, wherein one or more of the linker arms is selected from the group consisting of: —X—Y, —X—O—Y, —X—NH—Y, —X—N=Y, —X—NR—Y, X—CO—Y, —X—COO—Y, —X—OCO—Y, —X—NHCO—Y, —X—CONH—Y, —X—N=C(O—Y)$_2$, —X—NHCH(NH$_2$)—O—Y, —X—S—Y, —X—S—S—Y, —X—SO$_2$NH—Y and —X—NHSO$_2$—Y; wherein R is alkyl, alkenyl, aryl, arylalkyl or acyl; X is a saturated or an unsaturated hydrocarbon chain; Y is a solid-phase formed from a biocompatible polymer such as cellulose, polystyrene, polyamide, polyethersulfone, polyethyleneglycol, polypropyleneglycol, polyvinylalchol and polysiloxane.

In preferred embodiments, $R_1$ and $R_2$ are the aforementioned linker arms formed of hydrocarbons of varying lengths. These two linker arms can be the same or different, although for ease of synthesis, they will often be the same.

In an intermediate stage, i.e., before the dye compound is covalently linked to the solid support, the dye compound is modified to include at least one functional group, e.g., carboxyl, hydroxyl, amino, cyano, or halogen substituent, to facilitate covalent attachment to the solid-phase. Alternatively, the linker arm can be first attached to the solid-phase or the dye compound. Alternatively, both the dye compound and the solid-phase can be derivatized with the covalent attachment be formed somewhere in between the two.

Similarly, other preferred embodiments are those wherein $R_3$ is a single linker arm that is covalently bound to Q on one end and a solid support on another. As above, the $R_3$ linker is preferably a saturated or unsaturated hydrocarbon chain that can be otherwise functionalized. As above, the length of the hydrocarbon chain can vary quite extensively, but will preferably be about $C_{30}$ or fewer. The hydrocarbons can be straight-chain alkyl groups, or they can be functionalized or branched at various points along the hydrocarbon chain. As above, the linker arm will preferably be functionalized as by a carboxyl, hydroxyl, amino, cyano, or halogen substituent to permit covalent attachment to a solid-phase material.

The $R_3$ linker arm can be covalently bound to the fluorophore, chromophore, or phosphorescent portion of the molecule at various locations. Preferably, it will be positioned where it will least interfere with the boronic acid substituents.

Where $R_3$ is the sole linker arm, $R_1$ and $R_2$ are preferably lower alkyl substituents. As used herein, the term lower alkyl means $C_{1-12}$.

Embodiments of the present invention include compounds of Formula 1 where: Q is a fluorophore, chromophore, or a phosphorescent or luminescent moiety; $R_1$, $R_2$, and $R_3$ are independently selected from the group consisting of a linker arm and a non-linking substituent; and $R_4$, $R_5$, $R_6$, and $R_7$ are the same or different and are selected from the group consisting of hydrogen, alkyl, alkenyl, aryl, arylalkyl, substituted alkyl, acyl, alkyloxy, and halogen. Together, the substituents $R_4$ and $R_5$, and $R_6$ and $R_7$, respectively, can form condensed aromatic rings such as naphthalene, anthracene, and the like. As described above, a linker arm is a saturated or unsaturated hydrocarbon that can be derivatized with other functional groups, is about $C_{30}$ or fewer, and is covalently bound to a solid-phase material. A non-linking substituent is hydrogen or a saturated or unsaturated hydrocarbon of about $C_{20}$ or fewer and optionally further derivatized with other functional groups.

The biocompatible polymer can be a homopolymer or it can be a copolymer of two or more polymers. A dye can be covalently attached to an existing polymer, or the dye-polymer complex can be formed by a reaction between reactive monomers and a functional group on one or more linker arms of the dye.

The immobilized solid-phase dye can be built into a variety of sensor products, e.g., vessel, conduit, or bed. The solid-phase dye can be fixed in a product by conventional mechanical or chemical means. For example, the polymeric solid-phase portion of the solid-phase-dye complex can be affixed to a structural material such as a metal, glass, or polymer portion that forms a housing, vessel, conduit, or the like and through which the fluid under investigation is passed. Depending upon the choice of materials, these parts can be glued, fused, coextruded, cast, molded, or otherwise combined as by mechanical means, e.g., snaps, screws, slide-mounts, etc.

Further, the present invention is versatile in that the dye can be covalently linked to the solid-phase material before or after the solid-phase material is fabricated into the overall component product or a subcomponent of the product.

Relating to the preservation method of the sensor, the solution contacting the sensor may contain at least one polyol. A polyol-containing solution can be used to protect the sensor device during sterilization and storage.

EXAMPLES

1. Shinkai Mono-phenylboronate/Single-arm Type

The dye designated PZ-33, its synthesis, and a means for immobilizing it to a Cuprophan substrate are illustrated in FIG. 4.

PZ-33 is made with a linker arm attached to the nitrogen bridge between the benzene moiety and the anthracene moiety. The soluble dye senses saccharide over the physiologic range, but is somewhat sensitive to pH and ionic strength. The dye, both in solid-phase and soluble form, has limited stability when exposed to sterilization, high humidity, and high temperature.

When attached to a regenerated cellulose film (Cuprophan) via the linker arm, the dye retained saccharide sensitivity. However, the slope was less than the corresponding molecule in solution. The time response for binding glucose was very fast, less than a minute, but release was very slow. Sensitivity to shelf life and sterilization forces appears similar to soluble molecule.

Figure 6:
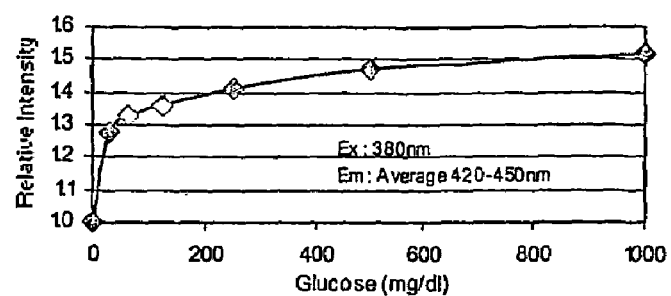
FIG. 6 is a Glucose Response curve for the compound synthesized and immobilized as shown in FIG. 5.

An analogous compound (G47) with a pyrene fluorophore was also synthesized. The dye (G47) with a single spacer or linker arm was synthesized and then immobilized on a regenerated cellulose film (Cuprophan). FIG. 5. The glucose response curve for the resulting sensor is shown in FIG. 6.

2 Shinkai Bis-phenylboronate/Double-arm Type

These dyes are made with two linker arms attached to the nitrogen bridges between the benzene moiety and the anthracene moiety. FIG. 7.

Dye with amino-terminated arms is synthesized from halomethylanthracene, phenyl boronic acid, and mono protected alkyldiamine as linker arm moiety. Dye with carboxyl-terminated arms is synthesized using amino acid t-butyl ester as linker arm.

Figure 9:
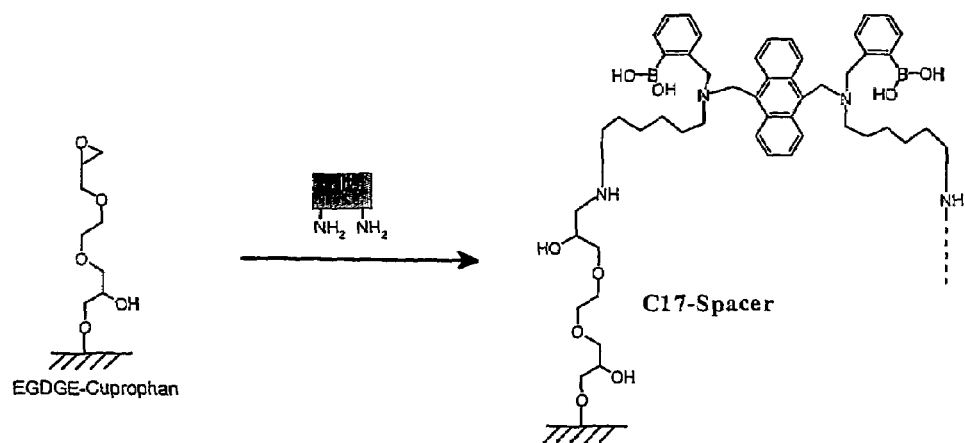
Figure 10:
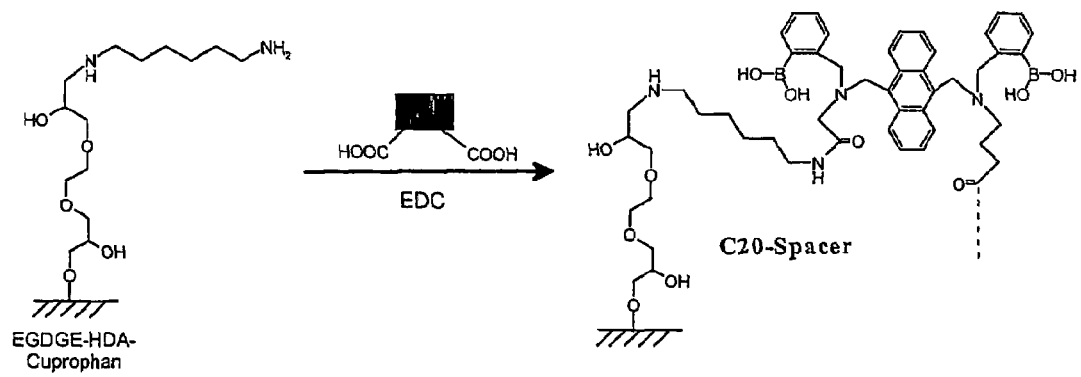

Glucose response of these dyes is greatly improved compared to the Shinkai mono-phenylboronate single-arm type dyes. Immobilization of these dyes is illustrated in FIGS. 8-10.

Figure 11:
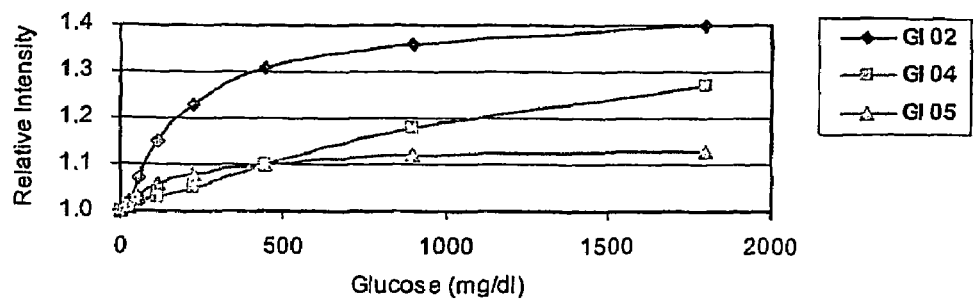
FIG. 11 is curve showing the Relative Intensity of several Bis-phenylboronate anthracene-containing Shinkai-type dyes.

Glucose response curves of some of these sensors were better than the mono-phenyl boronate/single-arm type. FIG. 11.

Figure 12:
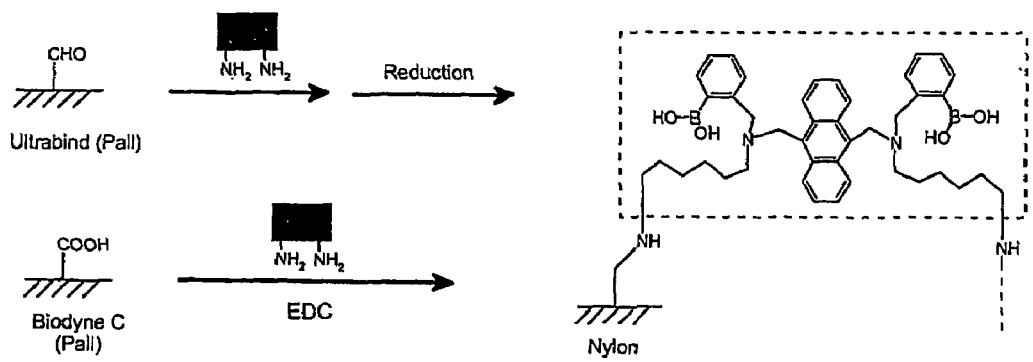
FIG. 12 is a schematic illustration for reacting a Bis-phenylboronate anthracene-containing Shinkai-type dye having an amino-terminal linker arm precursor with a nylon solid-phase material for immobilization.

Solid-phase is not restricted to regenerated cellulose. For example, bis-phenyl boronate/double-arm type dye can be effectively immobilized by covalent attachment to activated nylon membranes such as Ultrabind® or Biodyne® (Pall Corp.). FIG. 12. These immobilized saccharide sensor membranes had good glucose response.

Figure 13:
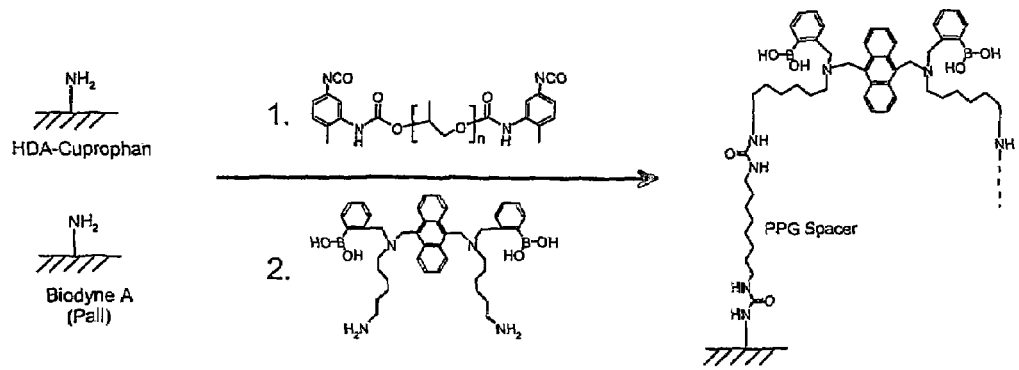
FIG. 13 is a synthetic scheme for immobilizing a Bis-phenylboronate Shinkai-type dye on a solid-phase material with a polypropylene glycol spacer between the dye and the spacer.

The distance between dye and solid-phase can be controlled by using different length of spacers. This distance affects the reactivity of dye with saccharide on solid-phase. The use of polypropyleneglycol (PPG) as a spacer is illustrated in FIG. 13.

Figure 14:
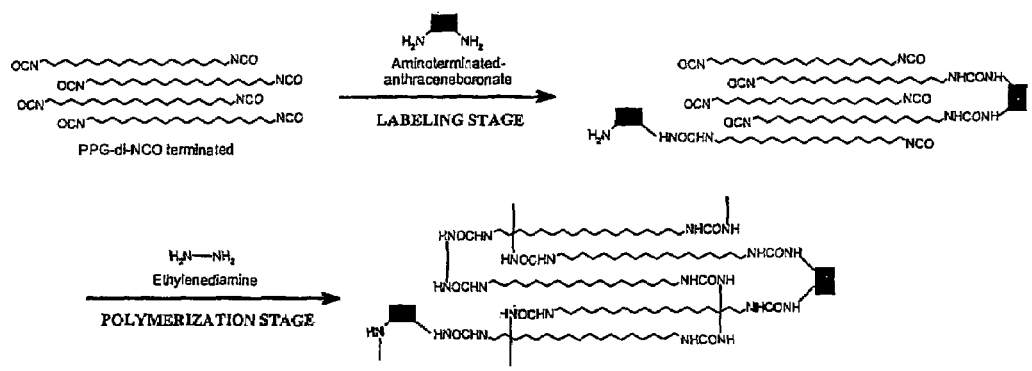
FIG. 14 illustrates immobilization by reacting a Shinkai-type dye having an amino-terminal linker arm precursor with a di-NCO terminated polypropylene glycol and subsequent cross-linking with ethylene diamine to produce an immobilized solid-phase Shinkai-type dye.

The dye can be built into polymers as shown in FIG. 14. Isocyanate terminated PPG was labeled with the dye, then cross linked by ethylenediamine, finally dye immobilized polymer was formed.

Figure 15:
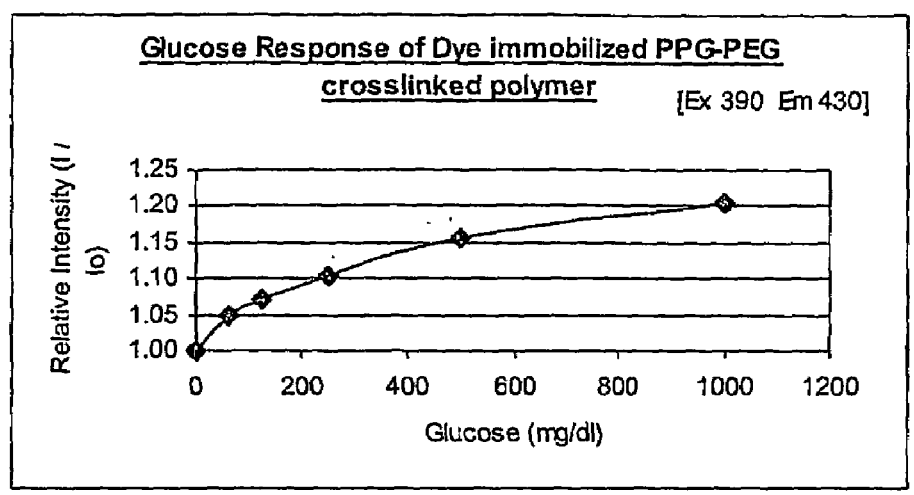
FIG. 15 shows the glucose response curve for the dye immobilized PPG-PEG crosslinked polymer.

As an alternate method, amino terminated PPG was cross linked by isocyanate terminated cross linker, labeled with the dye, then the reaction was terminated by the addition of ethylenediamine. One advantage of this latter method is that solid-phase can be molded in any shape or form. The formed dye-polymer complex can be shaped into film, membrane, or shaped particles, or it can be applied to a sensor well or fiber tip by inpour or dabbing. Dye-polymer complexes formed by this method had good glucose response. FIG. 15.

3. Shinkai Bis-phenylboronate/Single-arm Type

Figure 17:
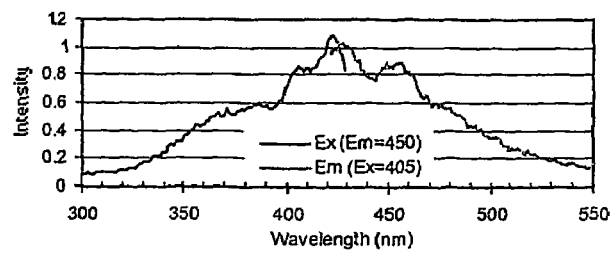
FIG. 17 illustrates the fluorescent property of the single-arm fluorophore sensor of FIG. 16.
Figure 18:
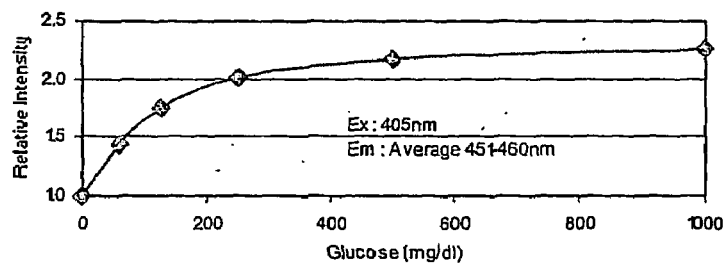
FIG. 18 shows the glucose response curve for the single-arm fluorophore of FIG. 16.

This class of dye has a single arm attachment of bis-phenylboronate dye. The dye has one linker arm covalently bonded directly to an aromatic ring of a fluorophore. In one embodiment, the dye has an available carboxyl group through which covalent immobilization is achieved. Anthracene carboxylic acid was derived from acetyl anthracene. The carboxyl group of the dye was attached to an amino activated solid-phase by condensation reaction using carbodiilide. FIG. 16. This Single-Arm Fluorophore Linked Sensor was immobilized on a membrane and demonstrated favorable fluorescent property as shown in FIG. 17. The glucose response curve of the Single Arm Fluorophore Linked Sensor immobilized on a membrane is shown in FIG. 18.

4. Improvement of Fluorescent Property

Introduction of an acyl group on the anthracene fluorophore improved the fluorescent property of the immobilized dye. The acetyl group was added to a substituted anthracene by a Friedel-Crafts reaction. Subsequent steps produced a bis-phenyl boronate type dye with two amino-terminated arms in the same manner as mentioned above. Immobilization via the amino-terminated linker arms to Cuprophan was carried out by a cyanogen-bromide activation method. FIG. 19.

Figure 20:
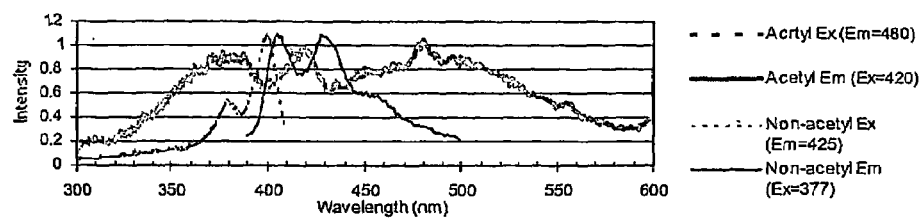
FIG. 20 shows the fluorescent property of the acetylated and nonacetylated anthracene dye of FIG. 19.

The resulting immobilized sensor had a better fluorescent property than the corresponding sensor without the acetyl group. The excitation and emission peaks were shifted to longer wavelengths and greater Stoke's shift. Immobilized sensor compounds having an emission peak of about 500 nm and an excitation peak below about 400 nm are suitable for an optical detection system, considering the properties of currently commercially available LEDs, optical filters, or photo detectors. FIG. 20.

Figure 21:
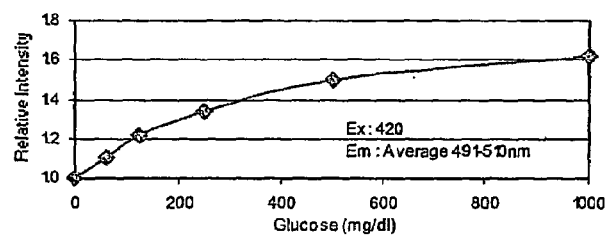
FIG. 21 shows the glucose response curve for the dye of FIG. 19.

This sensor also gave a good glucose curve over the physiologic range in blood. FIG. 21.

What is claimed is:

1. A compound of the formula:

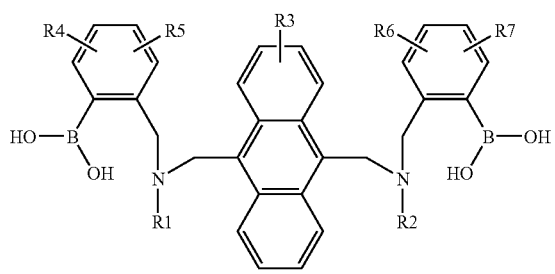

wherein:
at least one of R1 and R2 is a linker arm, and the other is independently selected from the group consisting of linker arms and non-linker substituents; where the linker arm is a saturated or unsaturated, substituted or unsubstituted, hydrocarbon of about $C_{30}$ or fewer, and is covalently bonded to a solid substrate; where the non-linker substituent is hydrogen, or a saturated or unsaturated, substituted or unsubstituted, hydrocarbon of about $C_{20}$ or fewer;

R3 is selected from the group consisting of halogen, acyl, alkyloxy, nitro, carboxylic acid, and carboxylic acid ester, and R4, R5, R6, and R7 are the same or different, and are selected from the group consisting of hydrogen, alkyl, alkenyl, aryl, arylalkyl, substituted alkyl, acyl, alkyloxy, and halogen.

2. The compound of claim 1, wherein said acyl group is acetyl.

3. The compound of claim 1, wherein the linker arm covalently bound to a solid substrate includes a polypropyleneglycol spacer between the saccharide dye and the solid substrate.

4. The compound according to claim 1, wherein the solid substrate is a biocompatible polymer selected from the group consisting of cellulose, polystyrene, polyamide, polyethersulfone, polyethyleneglycol, polypropyleneglycol, polyvinylalcohol, polysiloxane, nylon, and copolymers thereof.

5. The compound of claim 1, having a fluorescence excitation peak and emission peak upon saccharide conjugation, and wherein the excitation peak and the emission peak differ by at least about 40 nm.

6. The compound of claim 1, wherein relative intensity of fluorescence of the molecule upon saccharide conjugation is greater than about 1.5 across the physiological range of glucose concentration.

7. A compound of the formula:

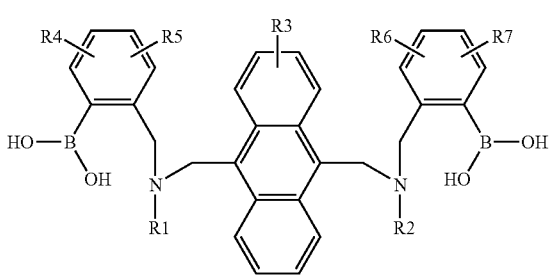

wherein
at least one of R1 and R2 is a linker arm, and the other is independently selected from the group consisting of linker arms and non-linker substituents; where the linker arm is a saturated or unsaturated, substituted or unsubstituted, hydrocarbon of about $C_{30}$ or fewer, and is covalently bonded to a solid substrate; where the non-linker substituent is hydrogen, or a saturated or unsaturated, substituted or unsubstituted, hydrocarbon of about $C_{20}$ or fewer;

and R4, R5, R6, and R7 are the same or different, and are selected from the group consisting of hydrogen, alkyl, alkenyl, aryl, arylalkyl, substituted alkyl, acyl, alkyloxy, and halogen.

8. The compound of claim 7, wherein the linker arm covalently bound to a solid substrate includes a polypropyleneglycol spacer between the saccharide dye and the solid substrate.

9. The compound according to claim 7, wherein the solid substrate is a biocompatible polymer selected from the group consisting of cellulose, polystyrene, polyamide, polyethersulfone, polyethyleneglycol, polypropyleneglycol, polyvinylalcohol, polysiloxane, nylon, and copolymers thereof.

10. The compound of claim 7, having a fluorescence excitation peak and emission peak upon saccharide conjugation, and wherein the excitation peak and the emission peak differ by at least about 40 nm.

11. The compound of claim 7, wherein relative intensity of fluorescence of the molecule upon saccharide conjugation is greater than about 1.5 across the physiological range of glucose concentration.

12. A compound of the formula:

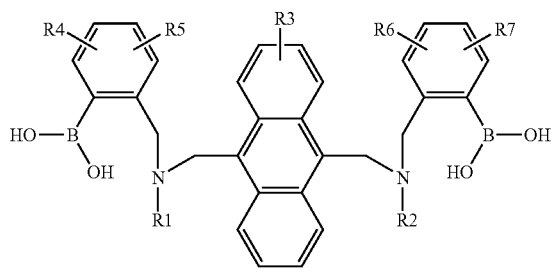

wherein:
R1 and R2 are the same or different, and are selected from the group consisting of hydrogen, and a saturated or unsaturated, substituted or unsubstituted, hydrocarbon of about $C_{20}$ or fewer;
and R4, R5, R6, and R7 are the same or different, and are selected from the group consisting of hydrogen, alkyl, alkenyl, aryl, arylalkyl, substituted alkyl, acyl, alkyloxy, and halogen; and
R8 is a linker-arm that is a saturated or unsaturated, substituted or unsubstituted, hydrocarbon of about $C_{30}$ or fewer.

13. The compound of claim 12, wherein said linker arm contains one or more functional groups selected from the group consisting of amide and ester.

14. The compound of claim 12, wherein the linker arm is covalently bound to a solid substrate, and the linker arm includes a polypropyleneglycol spacer between the saccharide dye and the solid substrate.

15. The compound according to claim 12, wherein the solid substrate is a biocompatible polymer selected from the group consisting of cellulose, polystyrene, polyamide, polyethersulfone, polyethyleneglycol, polypropyleneglycol, polyvinylalcohol, polysiloxane, nylon, and copolymers thereof.

16. The compound of claim 12, having a fluorescence excitation peak and emission peak upon saccharide conjugation, and wherein the excitation peak and the emission peak differ by at least about 40 nm.

17. The compound of claim 12, wherein relative intensity of fluorescence of the molecule upon saccharide conjugation is greater than about 1.5 across the physiological range of glucose concentration.

18. A method for immobilizing a compound on a solid substrate, comprising reacting an amino-terminated hydrocarbon with a solid substrate activated with a functional group selected from the group consisting of carboxyl, carbonyl, cyanogenbromide, epoxy, and isocyanate;

wherein the amino-terminated hydrocarbon is a compound of the formula:

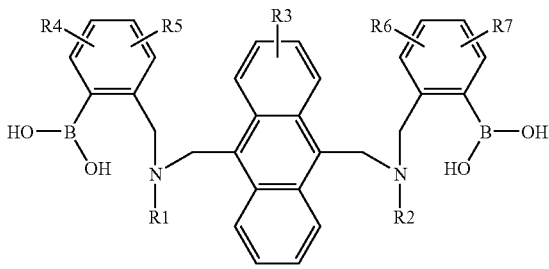

wherein:
R1 and R2 are independently selected from the group consisting of: hydrogen, amino-terminated hydrocarbons of about $C_{30}$ or fewer, and a hydrocarbon of about $C_{30}$ or fewer, such that at least one of R1 and R2 is an amino-terminated hydrocarbon;
R3 is selected from the group consisting of halogen, acyl, alkyloxy, nitro, carboxylic acid, and carboxylic acid ester; and
R4, R5, R6, and R7 are the same or different, and are independently selected from the group consisting of hydrogen, alkyl, alkenyl, aryl, arylalkyl, acyl, alkyloxy, and halogen.

19. The method of claim 18, wherein the activated polymer is cross-linked with ethylenediamine.

20. A sensor for detecting the concentration of saccharide in a biological fluid, said sensor comprising one or more compounds selected from the group consisting of compounds of claim 1.

21. A method for detecting the concentration of saccharide in a biological fluid comprising:
constructing a sensor comprising one or more compounds of the group consisting of the compounds of claim 1;
contacting the sensor with the biological fluid; and
measuring relative intensity of fluorescence of the compound.

22. A method for immobilizing a compound on a solid substrate, comprising reacting a carboxyl-terminated hydrocarbon with an amino-activated solid substrate, wherein the carboxyl-terminated hydrocarbon is a compound of the formula:

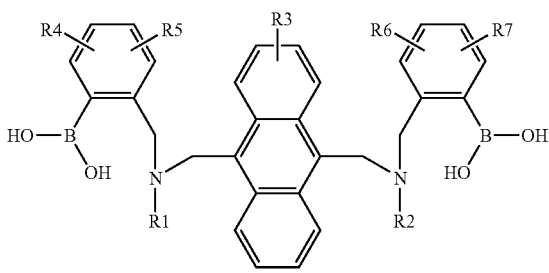

wherein:
R1 and R2 are independently selected from the group consisting of:
hydrogen, carboxyl-terminated hydrocarbons of about $C_{30}$ or fewer, and a hydrocarbon of about $C_{30}$ or fewer, such that at least one of R1 and R2 is a carboxyl-terminated-hydrocarbon;

R3 is selected from halogen, acyl, alkyloxy, nitro, carboxylic acid, and carboxylic acid ester; and R4, R5, R6, and R7 are the same or different, and are selected from the group consisting of hydrogen, alkyl, alkenyl, aryl, arylalkyl, acyl, alkyloxy, and halogen.

23. A method for immobilizing a compound on a solid substrate comprising reacting an amino-terminated hydrocarbon with a solid substrate that is activated with a functional group selected from the group consisting of carboxyl, carbonyl, cyanogenbromide, epoxy, and isocyanate, and wherein the amino-terminated hydrocarbon is a compound of the formula:

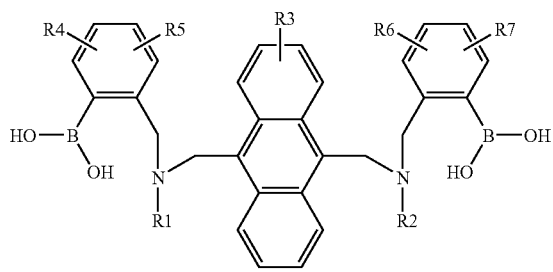

wherein:

R1 and R2 are the same or different, and are a hydrogen, or a saturated or unsaturated, substituted or unsubstituted, hydrocarbon of about $C_{20}$ or fewer;

and R4, R5, R6, and R7 are the same or different, and are selected from the group consisting of hydrogen, alkyl, alkenyl, aryl, arylalkyl, substituted alkyl, acyl, alkyloxy, and halogen; and R8 is an amino-terminated hydrocarbon of about $C_{30}$ or fewer.

24. A method for immobilizing a compound on a solid substrate comprising reacting a carboxyl-terminated hydrocarbon with an amino-activated solid substrate, wherein the carboxyl-terminated hydrocarbon is a compound of the formula:

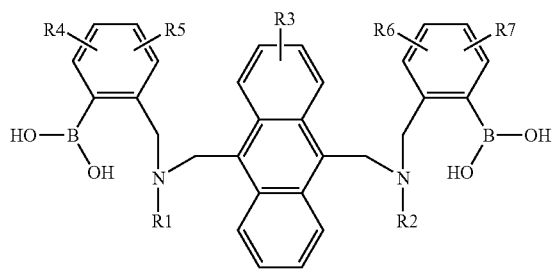

wherein:

R1 and R2 are the same or different, and are a hydrogen, or a saturated or unsaturated, substituted or unsubstituted, hydrocarbon of about $C_{20}$ or fewer;

and R4, R5, R6, and R7 are the same or different, and are selected from the group consisting of hydrogen, alkyl, alkenyl, aryl, arylalkyl, substituted alkyl, acyl, alkyloxy, and halogen; and R8 is a carboxyl-terminated-hydrocarbon of about $C_{30}$ or fewer.

25. A sensor for detecting the concentration of saccharide in a biological fluid, said sensor comprising one or more compounds selected from the group consisting of compounds of claim 7.

26. A method for detecting the concentration of saccharide in a biological fluid comprising:
constructing a sensor comprising one or more compounds of the group consisting of the compounds of claim 7;
contacting the sensor with the biological fluid; and
measuring relative intensity of fluorescence of the compound.

27. A sensor for detecting the concentration of saccharide in a biological fluid, said sensor comprising one or more compounds selected from the group consisting of compounds of claim 12.

28. A method for detecting the concentration of saccharide in a biological fluid comprising:
constructing a sensor comprising one or more compounds of the group consisting of the compounds of claim 12;
contacting the sensor with the biological fluid; and
measuring relative intensity of fluorescence of the compound.

* * * * *